United States Patent [19]

Myers

[11] 4,377,590

[45] Mar. 22, 1983

[54] DERIVATIVES OF AMPICILLIN AND AMOXICILLIN WITH BETA-LACTAMASE INHIBITORS

[75] Inventor: Robert F. Myers, East Lyme, Conn.

[73] Assignee: Pfizer Inc., New York, N.Y.

[21] Appl. No.: 376,487

[22] Filed: May 10, 1982

[51] Int. Cl.$^3$ .................... A61K 31/43; C07D 499/32
[52] U.S. Cl. ................................. 424/271; 260/239.1
[58] Field of Search ..................... 260/239.1; 424/271

[56] References Cited

U.S. PATENT DOCUMENTS

| | | | |
|---|---|---|---|
| 4,234,579 | 11/1980 | Barth | 424/246 |
| 4,244,951 | 1/1981 | Bigham | 424/250 |
| 4,287,181 | 9/1981 | Kellogg | 424/114 |

FOREIGN PATENT DOCUMENTS 2044255 10/1980 United Kingdom .

*Primary Examiner*—Natalie Trousof
*Assistant Examiner*—Vera C. Clarke
*Attorney, Agent, or Firm*—Charles J. Knuth; Albert E. Frost; J. Trevor Lumb

[57] ABSTRACT

Certain beta-lactamase inhibitors which have a beta-lactam ring as well as a carboxy group have been linked through their carboxy group to either the amino group of ampicillin, the amino group of amoxicillin or the phenolic hydroxy group of amoxicillin. This affords novel antibacterial agents.

21 Claims, No Drawings

DERIVATIVES OF AMPICILLIN AND AMOXICILLIN WITH BETA-LACTAMASE INHIBITORS

BACKGROUND OF THE INVENTION

This invention relates to the chemotherapy of bacterial infections. More particularly it relates to the chemotherapy of bacterial infections using certain new derivatives of ampicillin and amoxicillin.

Ampicillin and amoxicillin are two, well-known, penicillin antibiotics, which are widely used in medical practice today. Although both antibiotics have a reasonably broad spectrum of activity, both antibiotics suffer from the fact that they are susceptible to beta-lactamases. Accordingly both antibiotics tend to show weak activity against beta-lactamase producing microorganisms. One solution to this problem which has been developed is to co-administer a beta-lactamase inhibitor, such as penicillanic acid 1,1-dioxide (sulbactam), during a course of treatment with ampicillin or amoxicillin. See further U.S. Pat. No. 4,234,579. More recently, the antibacterial spectrum of ampicillin and amoxicillin has been expanded by making a bis-ester of methanediol, in which one of the hydroxy groups of the methanediol has been esterified using the carboxy group of ampicillin or amoxicillin, and the other hydroxy group has been esterified using the carboxy group of a beta-lactamase inhibitor such as sulbactam. See further U.S. Pat. No. 4,244,951 and published British patent application No. 2,044,255A.

In the novel antibacterial agents of the present invention, a beta-lactamase inhibitor which has a beta-lactam ring as well as a carboxy group (e.g. sulbactam) has been linked through its carboxy group to either the amino group of ampicillin, the amino group of amoxicillin or the phenolic hydroxy group of amoxicillin.

SUMMARY OF THE INVENTION

In its broadest sense, this invention provides novel antibacterial agents of the formula

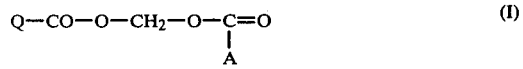

and the pharmaceutically-acceptable salts thereof, wherein the radical Q—CO—O— represents a radical of a beta-lactamase inhibitor (Q—CO—OH) which contains a beta-lactam ring as well as a carboxy group, and A is selected from the group consisting of

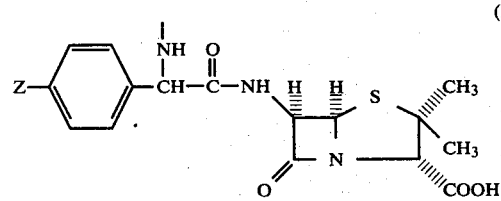

and

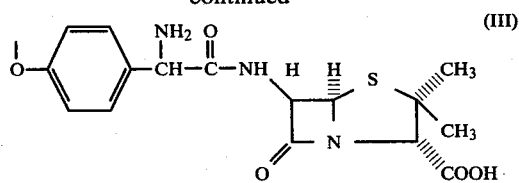

wherein Z is selected from the group consisting of hydrogen and hydroxy.

Typical examples of the beta-lactamase inhibitor radicals, Q—CO—O—, are

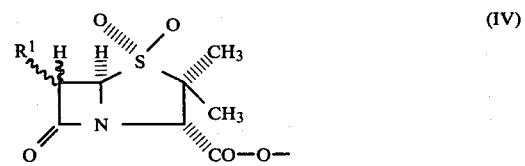

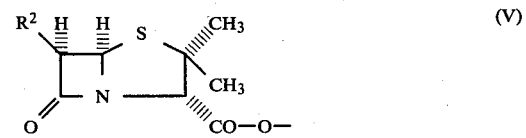

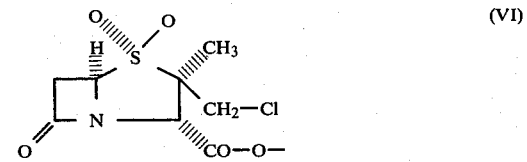

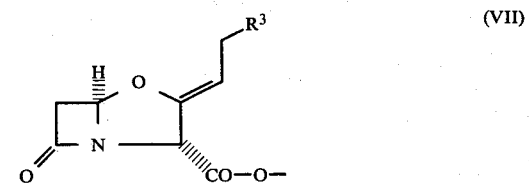

wherein
R$^1$ is selected from the group consisting of hydrogen and hydroxymethyl;
R$^2$ is selected from the group consisting of chloro, bromo and iodo; and
R$^3$ is selected from the group consisting of hydroxy and those radicals known to impart beta-lactamase inhibiting activity to clavulanic acid when attached to the corresponding position in clavulanic acid.

However, the preferred antibacterial agents of this invention are the compounds of formula I, wherein Q—CO—O— is of formula IV and the group R$^1$ is in the beta-configuration, and the pharmaceutically-acceptable salts thereof.

Also included within the scope of this invention are certain protected derivatives of ampicillin and amoxicillin, in which a halomethoxycarbonyl group has been attached to either the amino group of ampicillin, the amino group of amoxicillin or the phenolic hydroxy group of amoxicillin. These latter compounds are chemical intermediates to the antibacterial agents of formula I.

DETAILED DESCRIPTION OF THE INVENTION

This invention relates to derivatives of penicillanic acid, which is represented by the following structural formula

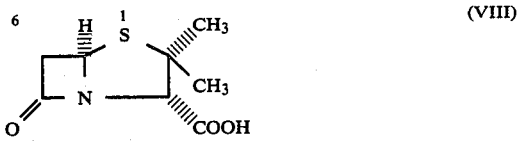

In formula VIII, broken line attachment of a substituent to the bicyclic nucleus indicates that the substituent is below the plane of the bicyclic nucleus and such a substituent is said to be in the alpha-configuration. Conversely, solid line attachment of a substituent to the bicyclic nucleus indicates that the substituent is attached above the plane of the nucleus and this latter configuration is referred to as the beta-configuration. Additionally, wavy line attachment of a substituent to the bicyclic nucleus indicates that the substituent is in the alpha-configuration or the beta-configuration or that a mixture is present.

Additionally, throughout this specification, whenever reference is made to a compond which has a 2-amino-2-(substituted)acetamido or 2-(substituted amino)-2-(substituted)acetamido group at the 6-position of a penicillanic acid derivative, it is to be understood that this refers to a compound in which said 2-amino-2-(substituted)acetamido or 2-(substituted amino)-2-(substituted)acetamido has the D-configuration.

In one method, the compounds of the formula I can be prepared from a compound of the formula

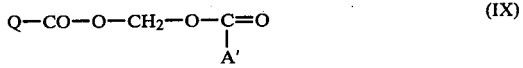

wherein Q is as defined previously and A' is selected from the group consisting of

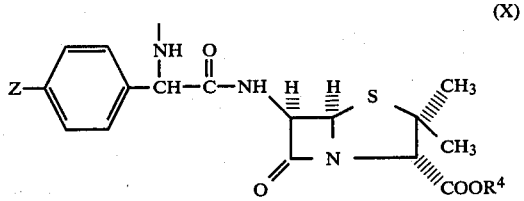

and

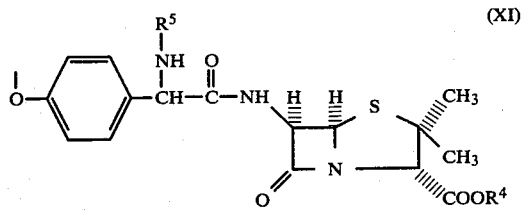

wherein Z is as defined previously, $R^4$ is a carboxy protecting group and $R^5$ is an amino protecting group, by removal of the protecting groups $R^4$ and $R^5$. A variety of groups known in the art for protecting carboxy groups in penicillin compounds can be used for $R^4$, and likewise a variety of groups known in the art for protecting amino groups can be used for $R^5$. Moreover, said protecting groups $R^4$ and $R^5$ are removed by the method normally used for that particular group.

However, when Q—CO—O— is of formula IV or VII, particularly useful groups for $R^4$ are benzyl and 4-nitrobenzyl, and particularly convenient groups for $R^5$ are benzyloxycarbonyl and 4-nitrobenzyloxycarbonyl.

When benzyl and 4-nitrobenzyl are used for $R^4$ and benzyloxycarbonyl and 4-nitrobenzyloxycarbonyl are used for $R^5$, these groups can be removed using a conventional hydrogenolysis reaction, and this hydrogenolysis is carried out in conventional fashion for this type of transformation. Thus, a solution of a compound of the formula IX is stirred or shaken under an atmosphere of hydrogen, or hydrogen mixed with an inert diluent such as nitrogen or argon, in the presence of a catalytic amount of a hydrogenolysis catalyst. Convenient solvents for this hydrogenolysis are lower-alkanols, such as methanol and isopropanol; ethers, such as tetrahydrofuran and dioxan; low molecular weight esters, such as ethyl acetate and butyl acetate; chlorinated hydrocarbons, such as chloroform and dichloromethane; water; and mixtures of these solvents. However, it is usual to choose conditions under which the starting material is soluble. The hydrogenolysis is usually carried out at room temperature and at a pressure from about 7 to about 70 psig. Typical hydrogenolysis catalysts are palladium and platinum, and a particularly suitable catalyst is palladium suspended on an inert support, e.g. 5–10% palladium-on-carbon. When 5–10% palladium-on-carbon is used, it is usually present in an amount from about 50 percent by weight based on the starting material up to an amount double the weight of the starting material, although larger amounts can be used. The reaction commonly takes a few hours, after which the compound of the formula I, is recovered by conventional means. When A is of formula II, the compound of formula I can be recovered simply by filtration, followed by partitioning of the filtrate between water and a volatile, water immiscible organic solvent at an acidic pH, separation of the layers, and evaporation of the organic layer. When A is of formula III, the compound of formula I can be recovered by filtration, followed by evaporation of the solvent to low volume, addition of a non-solvent and filtration. The compounds of formula I can be purified by conventional methods for beta-lactam compounds. For example, the compounds of formula I can be purified by gel filtration on sephadex, or by recrystallization.

When Q—CO—O— is of formula V or VI in a compound of the formula IX, convenient groups for $R^4$ are groups of the formula —N=CH—Ar, wherein Ar is phenyl or 2-furyl. The —N=CH—Ar groups can be removed by treating the compound of formula IX with a variety of nucleophilic reagents, such as sodium iodide or sodium thiocyanate, according to well-known procedures. See, for example, Fosker et al., Journal of the Chemical Society (London), Part (c), 1917 (1971).

When Q—CO—O— is of formula V or VI in a compound of the formula IX, convenient groups for $R^5$ are 1-methyl-2-alkoxycarbonylvinyl groups, especially the 1-methyl-2-methoxycarbonylvinyl group (—C[CH$_3$]=CH—COOCH$_3$). 1-Methyl-2-alkoxycarbonylvinyl groups can be removed by standard methods, i.e. by exposing the compound of formula IX to an aqueous or partially aqueous solvent system at a pH below about 3.

The compounds of formula IX can be obtained by coupling a compound of the formula

$$Q-CO-OM \qquad (XII)$$

with a compound of the formula

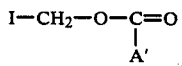

$$I-CH_2-O-\underset{\underset{A'}{|}}{C}=O \qquad (XIII)$$

wherein Q—CO—OM is a carboxylate salt of the beta-lactamase inhibitor Q—CO—OH (i.e. M is a carboxylate salt forming cation) and A' is as defined previously. A variety of cations can be used to form the carboxylate salt in the compound of formula XII, but salts which are commonly used include: alkali metal salts, such as sodium and potassium salts; alkaline earth metal salts, such as calcium and barium salts; tertiary amine salts, such as trimethylamine, triethylamine, tributylamine, diisopropylethylamine; N-methylmorpholine, N-methylpiperidine, N-methylpyrrolidine and N,N'-dimethylpiperazine; and quaternary ammonium salts such as tetra-(n-butyl)ammonium salts.

The reaction between a compound of formula XII and a compound of formula XIII is usually carried out by contacting the reagents in an organic solvent, at a temperature in the range from about −10° to about 80° C., and preferably from 25° to 50° C. The compounds of formula XII and XIII are usually contacted in substantially equimolar proportions, but an excess of either reagent, for example up to a ten-fold excess, can be used. A wide variety of solvents can be used, but it is usually advantageous to use a relatively polar solvent, since this has the effect of speeding up the reaction. Typical solvents which can be used include N,N-dimethylformamide, N,N-dimethylacetamide, N-methylpyrrolidone, and hexamethylphosphoramide. The reaction time varies according to a number of factors, but at about 25° C. reaction times from 0.5 to 24 hours are commonly used.

The compound of formula IX is isolated in conventional fashion. When a water-miscible solvent is used, it is usually sufficient simply to dilute the reaction medium with an excess of water. The product is then extracted into a volatile, water-immiscible solvent, such as ethyl acetate, and then the product is recovered by solvent evaporation. When a water-immiscible solvent is used, it is usually sufficient to wash the solvent with water, and then recover the product by solvent evaporation. The compound of formula IX can be purified by well-known methods, such as recrystallization or chromatography, but due regard must be given to the lability of the beta-lactam ring system.

For the beta-lactamase inhibitors of the formula Q—CO—OH, and their conversion into salts of the formula Q—CO—OM, see, for example, U.S. Pat. Nos. 4,234,579, 4,287,181 and 4,110,165, Belgian Pat. No. 887,173, published Netherlands patent application No. 81/00209 and published European patent application No. 13,617.

The compounds of the formula XIII can be prepared from the corresponding compound of the formula

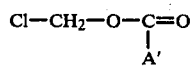

$$Cl-CH_2-O-\underset{\underset{A'}{|}}{C}=O \qquad (XIV)$$

wherein A' is as previously defined. This conversion is usually carried out by contacting the compound of formula XIV with an excess, e.g. a ten-fold excess, of sodium iodide in acetone. The reaction proceeds quite quickly at about room temperature, and it is usually substantially complete within a few hours. At the end of the reaction, the reaction medium can be diluted with a water-immiscible, volatile, organic solvent, such as chloroform, and this solution is washed with water. After drying, the organic solvent solution is evaporated to give the compound of formula XIII. In most instances, the compound of formula XIII so obtained is pure enough for reaction with a compound of formula XII. However, if desired, a compound of formula XIII can be purified by standard methods for penicillin compounds.

The compounds of formula XIV can be prepared from the corresponding compound of formula A'H, wherein A' is as previously defined, by acylation with chloromethyl chloroformate (Cl—CH$_2$—O—C(=O)—Cl). In practice the compound of formula A'H is usually treated with about an equimolar amount of chloromethyl chloroformate, in an inert solvent, such as tetrahydrofuran, in the presence of about one molar equivalent of a tertiary amine, such as diisopropylethylamine. After the reaction is complete (1 to 3 hours at room temperature) the product is recovered by diluting the reaction medium with a water-miscible, volatile, organic solvent, such as ethyl acetate, washing this diluted solution with water, drying the solution and then evaporating the solution in vacuo to give the compound of formula XIV. The compound of formula XIV can be purified by conventional methods for penicillin compounds, e.g. chromatography.

Chloromethyl chloroformate is prepared by photochemical chlorination of methyl chloroformate using known methods.

The compounds of formula A'H, wherein A' is of formula X, are prepared by a three-step sequence which comprises: (a) protecting the amino group of ampicillin or amoxicillin as an enamine by reaction with methyl acetoacetate; (b) attaching the group $R^4$ to the carboxy group of the product of step (a); and (c) removing the enamine protecting group from the amino group. Steps (a), (b) and (c) are all carried out using standard methods.

The compounds of formula A'H, wherein A' is of formula XI, can be prepared from the appropriate compound of formula A'H, wherein A' is of formula X and Z is hydroxy, simply by attaching the requisite amino protecting group to said compound of formula A'H, wherein A' is of formula X and Z is hydroxy. The amino protecting group is attached in conventional fashion.

The compounds of formula I, wherein A is of formula III have a basic amino group, and therefore they will form acid addition salts. These acid addition salts are considered to be within the scope and purview of this invention. Said acid addition salts are prepared by standard methods for penicillin compounds, for example by combining a solution of the compound of formula I in a suitable solvent (e.g. water, acetone, methanol, ethanol or butanol) with a solution containing a stoichiometric equivalent of the appropriate acid. If the salt precipitates, it is recovered by filtration. Alternatively, it can be recovered by evaporation of the solvent, or, in the case of aqueous solutions, by lyophilization. Of particular value are the sulfate, hydrochloride, hydrobromide, nitrate, phosphate, citrate, tartrate, pamoate, perchlorate, sulfosalicylate and 4-toluenesulfonate salts.

The compounds of formula I have a carboxy group in the A moiety and therefore they will form base salts. These base salts are to be considered within the scope and purview of this invention. The base salts are prepared by standard methods for penicillin compounds, for example by contacting the acidic and basic components in a stoichiometric ratio, in an aqueous, non-aqueous or partially aqueous medium, as appropriate. They are then recovered by filtration, by precipitation with a non-solvent followed by filtration, by evaporation of the solvent, or, in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine, p-toluidine and octylamine; secondary amines, such as diethylamine, N-methylaniline, morpholine, pyrrolidine and piperidine; tertiary amines, such as triethylamine, N,N-dimethylaniline, N-ethylpiperidine, N-methylmorpholine and 1,5-diazabicyclo[4.3.0]non-5-en; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; and bicarbonates, such as sodium bicarbonate and potassium bicarbonate.

When contemplating therapeutic use for a salt of an antibacterial compound of this invention, it is necessary to use a pharmaceutically-acceptable salt; however, salts other than these can be used for a variety of purposes. Such purposes include isolating and purifying particular compounds, and interconverting pharmaceutically-acceptable salts and their non-salt counterparts.

The compounds of formula I possess in vivo antibacterial activity in mammals, and this activity can be demonstrated by standard techniques for penicillin compounds. For example, the compound of formula I is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compound is assessed by counting the number of survivors which have been challenged by the bacterium and also have received the compound of formula I. The compounds of formula I can be administered by both the oral (p.o.) and subcutaneous (s.c.) route.

The in vivo activity of the antibacterial compounds of this invention makes them suitable for the control of bacterial infections in mammals, including man, by both the oral and parenteral modes of administration. The compounds are useful in the control of infections caused by susceptible bacteria in human subjects.

After administration to a mammalian subject by both the oral and parenteral route, a compound of formula I breaks down into the beta-lactamase inhibitor, Q—CO—OH, and ampicillin or amoxicillin, depending on the meaning of A. When A is of formula II, wherein Z is hydrogen, the beta-lactamase inhibitor and ampicillin are liberated; when A is of formula II, wherein Z is hydroxy, the beta-lactamase inhibitor and amoxicillin are liberated; and when A is of formula III, the beta-lactamase inhibitor and amoxicillin are liberated. Thus the compounds of formula I will find use in the control of bacterial infections caused by microorganisms which are susceptible to a 1:1 mixture of the particular beta-lactamase inhibitor, Q—CO—OH, and either ampicillin or amoxicillin. For example, the compounds of formula I will find use against susceptible strains of *Escherichia coli* and *Staphylococcus aureus*.

In determining whether a particular strain of *Escherichia coli* or *Staphylococcus aureus* is sensitive to a given compound of formula I, the minimum inhibitory concentration (MIC) of a 1:1 mixture of the beta-lactamase inhibitor, Q—CO—OH, which will be liberated on cleavage and either ampicillin or amoxicillin can be measured. The MIC's can be measured by the procedure recommended by the International Collaborative Study on Antibiotic Sensitivity Testing (Ericcson and Sherris, *Acta. Pathologica et Microbiologia* Scandinav, Suppl. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye.

When using an antibacterial compound of this invention, or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and severity of the patient's symptoms. The compounds of this invention will normally be used orally at dosages in the range from 20 to about 100 mg. per kilogram of body weight per day, and parenterally at dosages from about 10 to about 100 mg. per kilogram of body weight per day, usually in divided doses. In some instances it may be necessary to use doses outside these ranges.

The following examples and preparations are provided solely for further illustration. Nuclear magnetic resonance spectra (NMR) were measured for solutions in deuterium oxide ($D_2O$), deuterated chloroform ($CDCl_3$), deuterated acetone ($CD_3COCD_3$) or deuterated dimethyl sulfoxide (DMSO-$d_6$), and peak positions are reported in parts per million downfield from tetramethylsilane. The following abbreviations for peak shapes are used: s, singlet; d, doublet; t, triplet; q, quartet; m, multiplet. Additionally, in the examples and preparations that follow, whenever reference is made to a tetrabutylammonium group, it is to be appreciated that said butyl moieties are n-butyl moieties ($CH_3CH_2CH_2CH_2$—).

EXAMPLE 1

6-(2-[1,1-Dioxopenicillanoyloxymethoxycarbonylamino]-2-phenylacetamido)penicillanic Acid A mixture of 1.3 g. of benzyl 6-(2-[1,1-dioxopenicillanoyloxymethoxycarbonylamino]-2-phenylacetamido)penicillanate, 8.0 g. of a 50% suspension of 5% palladium-on-carbon in water, 125 ml. of tetrahydrofuran and 68 ml. of water was shaken under an atmosphere of hydrogen at ca. 50 psig for 1.25 hours. The mixture was then filtered and the filtrate was concentrated to ca. 100 ml. To this was then added 200 ml. of ethyl acetate, and the pH was adjusted to 2.5 with 2 N hydrochloric acid. The ethyl acetate layer was removed, and the aqueous layer was further extracted with ethyl acetate. The ethyl acetate solutions were combined, dried ($Na_2SO_4$) and concentrated to ca. 5 ml. This latter solution was added dropwise, with stirring, to 100 ml. of diethyl ether and the solid which precipitated was recovered by filtration to give 0.43 g. of the title compound as a white solid. A second crop (0.33 g.) was obtained by evaporating the filtrate to small volume, re-adding to diethyl ether and recovering the precipitate.

The NMR spectrum (in DMSO-$d_6$) showed absorptions at 7.3 (s, 5H), 6.0–5.3 (m, 5H), 5.1 (m, 1H), 4.2 (s, 2H), 3.4–3.2 (m, 2H) and 1.5–1.3 (m, 12H) ppm.

EXAMPLE 2

6-(2-[1,1-Dioxopenicillanoyloxymethoxycarbonylamino]-2-[4-hydroxyphenyl]acetamido)penicillanic Acid A mixture of 1.5 g. of benzyl 6-(2-[1,1-dioxopenicillanoyloxymethoxycarbonylamino]-2-[4-hydroxyphenyl]acetamido)penicillanate, 5.0 g. of a 50% suspension of 5% palladium-on-carbon in water, 125 ml. of tetrahydrofuran and 75 ml. of water was shaken under an atmosphere of hydrogen at ca. 50 psig for 1 hour. At this point, an additional 3 g. of the 50% suspension of 5% palladium-on-carbon in water was added and the mixture was hydrogenated for an additional 45 minutes, and then finally an additional 1.0 g. of the 50% suspension of 5% palladium-on-carbon in water was added and the mixture was hydrogenated for a further 30 minutes. The product was isolated in the same manner as Example 1, giving 0.82 g. of the title compound as a white solid.

The NMR spectrum (in $CD_3COCD_3/D_2O$) showed absorptions at 7.3 (d, 2H), 6.8 (d, 2H), 5.9 (d of d, 2H), 5.6 (d, 1H), 5.5 (d, 1H), 5.4 (s, 1H), 5.0 (m, 1H), 4.4(s, 1H), 4.3 (s, 1H), 3.9–3.2 (m, 2H) and 1.7–1.2 (m, 12H) ppm.

EXAMPLE 3

6-(2-[1,1-Dioxopenicillanoyloxymethoxycarbonylamino]-2-phenylacetamido)penicillanic Acid At atmospheric pressure, 0.15 g. of 10% palladium-on-carbon was hydrogenated in 15 ml. of tetrahydrofuran. To this mixture was added 0.15 g. of 4-nitrobenzyl 6-(2-[1,1-dioxopenicillanoyloxymethoxycarbonylamino]-2-phenylacetamido)penicillanate in 0.5 ml. of tetrahydrofuran, and then this mixture was hydrogenated at atmospheric pressure until 3 molar equivalents of hydrogen had been consumed. The reaction mixture was filtered and the pH of the filtrate was lowered to 3.0. The bulk of the tetrahydrofuran was removed by evaporation in vacuo and 20 ml. of ethyl acetate was added. The pH was raised to 9.5 and the ethyl acetate layer was removed and discarded. Fresh ethyl acetate was added and the pH was lowered to 3.5. The ethyl acetate layer was removed, dried ($MgSO_4$) and evaporated in vacuo to give 0.05 g. of the title compound as a light yellow foam.

EXAMPLE 4

6-(2-[1,1-Dioxopenicillanoyloxymethoxycarbonylamino]-2-[4-hydroxyphenyl]acetamido)penicillanic Acid Hydrogenation of 4-nitrobenzyl 6-(2-[1,1-dioxopenicillanoyloxymethoxycarbonylamino]-2-[4-hydroxyphenyl]acetamido)penicillanate according to the procedure of Example 3 affords the title compound.

EXAMPLE 5

6-(2-[1,1-Dioxo-6-beta-hydroxymethylpenicillanoyloxymethoxycarbonylamino]-2-[4-hydroxyphenyl]acetamido)penicillanic Acid A mixture of 0.57 g. of benzyl 6-(2-[1,1-dioxo-6-beta-hydroxymethylpenicillanoyloxymethoxycarbonylamino]-2-[4-hydroxyphenyl]penicillanate, 1.5 g. of a 50% suspension of 5% palladium-on-carbon in water, 15 ml. of dichloromethane and 15 ml. of isopropanol was shaken under an atmosphere of hydrogen at ca. 50 psig for 1.5 hours. An additional 1.0 g. of the 50% suspension of 5% palladium-on-carbon in water was added and the hydrogenation was continued for a further 2.0 hours. At this point, the reaction mixture was filtered and the filtrate was concentrated in vacuo to give an oil. The oil was triturated with diethyl ether to give 0.24 g. of the title compound as a white solid.

The infrared spectrum (KBr disc) showed a strong absorption at 1777 $cm^{-1}$.

EXAMPLE 6

6-(2-[1,1-Dioxo-6-beta-hydroxymethylpenicillanoyloxymethoxycarbonylamino]-2-phenylacetamido)penicillanic Acid Hydrogenation of benzyl 6-(2-[1,1-dioxo-6-betahydroxymethylpenicillanoyloxymethoxycarbonylamino]-2-phenylacetamido)penicillanate according to the procedure of Example 5 affords the title compound.

EXAMPLE 7

6-(2-Amino-2-[4-(1,1-dioxopenicillanoyloxymethoxycarbonyloxy)phenyl]acetamido)penicillanic Acid Following the procedure of Example 5, 0.40 g. of benzyl 6-(2-benzyloxycarbonylamino)-2-[4-(1,1-dioxopenicillanoyloxymethoxycarbonyloxy)phenyl]acetamido)penicillanate was hydrogenated using 1.5 g. of 10% palladium-on-carbon. This afforded 0.2 g. of the title compound as a white solid.

EXAMPLE 8

6-(2-Amino-2-[4-(1,1-dioxo-6-betahydroxymethylpenicillanoyloxymethoxycarbonyloxy)phenyl]acetamido)penicillanic Acid Hydrogenation of 4-nitrobenzyl 6-(2-benzyloxycarbonylamino-2-[4-(1,1-dioxo-6-beta-hydroxymethylpenicillanoyloxymethoxycarbonyloxy)phenyl]acetamido)penicillanate according to the procedure of Example 5 affords the title compound.

EXAMPLE 9

Sodium 6-(2-[1,1-Dioxopenicillanoyloxymethoxycarbonylamino]-2-[4-hydroxyphenyl]acetamido)penicillanate To a stirred solution of 0.031 g. of sodium bicarbonate in 5 ml. of water, at ice-bath temperature, was added 0.25 g. of 6-(2-[1,1-dioxopenicillanoyloxymethoxycarbonylamino]-2-[4-hydroxyphenyl]acetamido)penicillanic acid. Stirring was continued for 5 minutes. The mixture was then filtered and the filtrate was lyophilized to give 0.19 g. of the title compound.

EXAMPLE 10

Benzyl 6-(2-[1,1-Dioxopenicillanoyloxymethoxycarbonylamino]-2-phenylacetamido)penicillanate To a stirred solution of 2.8 g. of tetrabutylammonium penicillanate 1,1-dioxide in 30 ml. of N,N-dimethylformamide, under nitrogen, at −10° C., was added 3.08 g. of benzyl 6-(2-iodomethoxycarbonylamino-2-phenylacetamido)penicillanate. Stirring was continued for 30 minutes and 300 ml. of ethyl acetate and 100 ml. of saturated sodium chloride were added. The ethyl acetate layer was removed, washed with water and saturated sodium chloride solution, dried (Na$_2$SO$_4$) and evaporated in vacuo. This afforded 2.39 g. of the title compound as a yellow foam.

The NMR spectrum of the product (in CDCl$_3$) showed absorptions at 7.3 (s, 10H), 6.9 (d, 1H), 6.6 (d, 1H), 6.0–5.2 (m, 5H), 5.2 (s, 2H), 4.6 (t, 1H), 4.4 (s, 2H), 3.4 (d, 2H), 1.5 (bs, 6H), 1.4 (s, 3H) and 1.3 (s, 3H) ppm.

EXAMPLE 11

Benzyl 6-(2-[1,1-Dioxopenicillanoyloxymethoxycarbonylamino]-2-[4-hydroxyphenyl]acetamido)penicillanate Reaction of 2.8 g. of tetrabutylammonium penicillanate, 1,1-dioxide with 3.19 g. of benzyl 6-(2-iodomethoxycarbonylamino-2-[4-hydroxyphenyl]acetamido)-penicillanate, using the procedure of Example 10, gave the title product as a sticky solid. It was dissolved in ethyl acetate and the ethyl acetate solution was added dropwise, with stirring, to an excess of diethyl ether. The solid which precipitated was recovered by filtration to give 2.95 g. of the title compound as a white solid.

The NMR spectrum of the product (in CD$_3$COCD$_3$) showed absorptions at 7.8 (s, 1H), 7.3 (s, 5H), 7.3 and 6.8 (d of d, 4H), 6.0–5.2 (m, 5H), 5.2 (s, 2H), 4.8 (d of d, 1H), 4.3 and 4.25 (s and s, 2H), 3.6–3.3 (m, 2H), 1.5 (s, 3H), 1.4 (s, 3H), 1.3 (s, 3H) and 1.25 (s, 3H) ppm.

EXAMPLE 12

4-Nitrobenzyl 6-(2-[1,1-Dioxopenicillanoyloxymethoxycarbonylamino]-2-phenylacetamido)penicillanate To a solution of 1.21 g. of sodium iodide in 50 ml. of N,N-dimethylformamide was added 0.68 g. of sodium penicillanate 1,1-dioxide and 1.55 g. of 4-nitrobenzyl 6-(2-chloromethoxycarbonylamino-2-phenylacetamido)penicillanate and the resulting mixture was stirred under nitrogen at room temperature for 23 hours. The reaction mixture was poured into a stirred mixture of 400 ml. of ethyl acetate and 100 ml. of brine. The ethyl acetate layer was removed and it was washed successively with water, 50% saturated sodium bicarbonate, water and brine. The dried ethyl acetate solution was then evaporated in vacuo to give 1.77 g. of a white solid. Chromatography of 1.02 g. of the latter solid on silica gel, eluting with ethyl acetate-hexane gave 0.33 g. of the title compound.

The NMR spectrum (CDCl$_3$) showed absorptions at 8.2 (d, 2H), 7.5 (d, 2H), 7.4 (s, 5H), 6.9 (broad d, 1H), 6.6 (broad d, 1H), 5.9–5.2 (m, 7H), 4.6 (t, 1H), 4.4 (s, 1H), 3.4 (d, 2H) and 1.6–1.1 (m, 12H) ppm. The IR spectrum (KBr disc) showed a strong absorption at 1797 cm$^{-1}$.

EXAMPLE 13

4-Nitrobenzyl 6-(2-[1,1-Dioxopenicillanoyloxymethoxycarbonylamino]-2-[4-hydroxyphenyl]acetamido)penicillanate Reaction of 4-nitrobenzyl 6-(2-chloromethoxycarbonylamino-2-[4-hydroxyphenyl]acetamido)penicillanate with sodium iodide and sodium penicillanate 1,1-dioxide, according to the procedure of Example 12, affords the title compound.

EXAMPLE 14

Benzyl 6-(2-[1,1-Dioxo-6-beta-hydroxymethylpenicillanoyloxymethoxycarbonylamino]-2-[4-hydroxyphenyl]acetamido)penicillanate Reaction of 0.46 g. of tetrabutylammonium 6-betahydroxymethylpenicillanate 1,1-dioxide with 0.64 g. of benzyl 6-(2-iodomethoxycarbonylamino-2-[4-hydroxyphenyl]acetamido)penicillanate, using the procedure of Example 10, gave 0.57 g. of the title compound.

The NMR spectrum (CD$_3$COCD$_3$) showed absorptions at 7.3 (s, 5H), 7.2 (d, 2H), 6.7 (d, 2H), 6.0–5.3 (m, 5H), 5.2 (s, 2H), 4.9 (d, 1H), 4.6–4.0 (m, 5H) and 1.6–1.2 (m, 12H) ppm.

EXAMPLE 15

Benzyl 6-(2-[1,1-Dioxo-6-beta-hydroxymethylpenicillanoyloxymethoxycarbonylamino]-2-phenylacetamido)penicillanate Reaction of tetrabutylammonium 6-beta-hydroxymethylpenicillanate 1,1-dioxide with benzyl 6-(2-iodomethoxycarbonylamino-2-phenylacetamido)penicillanate, according to the procedure of Example 10, affords the title compound.

EXAMPLE 16

Benzyl 6-(2-Benzyloxycarbonylamino-2-[4-(1,1-dioxopenicillanoyloxymethoxycarbonyloxy)phenyl]acetamido)penicillanate Reaction of 2.0 g. of benzyl 6-(2-benzyloxycarbonylamino-2-[4-iodomethoxycarbonyloxyphenyl]acetamido)penicillanate with 1.5 g. of tetrabutylammonium penicillanate 1,1-dioxide in 5 ml. of N,N-dimethylformamide, according to the procedure of Example 10, gave 1.2 g. of the title compound.

The NMR spectrum of the product (CD$_3$COCD$_3$) showed absorptions at 8.0 (broad d, 1H), 7.6–7.0 (m), 6.0 (q, 2H), 5.7–4.8 (m, 10H), 4.5 (s, 1H), 4.4 (s, 1H), 3.6–3.2 (m, 2H) and 1.7–1.2 (m, 12H) ppm.

EXAMPLE 17

4-Nitrobenzyl 6-(2-[4-Nitrobenzyloxycarbonylamino]-2-[4-(1,1-dioxo-6-beta-hydroxymethylpenicillanoyloxymethoxycarbonyloxy)phenyl]acetamido)penicillanate Reaction of tetrabutylammonium 6-beta-hydroxymethylpenicillanate 1,1-dioxide with 4-nitrobenzyl 6-(2-[4-nitrobenzyloxycarbonylamino]-2-[4-iodomethoxycarbonyloxyphenyl]acetamido)penicillanate, using the procedure of Example 10, affords the title compound.

EXAMPLE 18

Benzyl 6-(2-Iodomethoxycarbonylamino-2-phenylacetamido)penicillanate

Under a nitrogen atmosphere, at room temperature, 7.5 g. of sodium iodide was dissolved in 25 ml. of acetone. To this solution was then added, with stirring, 2.65 g. of benzyl 6-(2-chloromethoxycarbonylamino-2-phenylacetamido)penicillanate. Stirring was continued for one hour and then the reaction mixture was poured into 200 ml. of chloroform. The chloroform solution was washed with water followed by saturated sodium chloride solution. The dried (Na$_2$SO$_4$) chloroform solution was evaporated in vacuo to give 3.08 g. of the title compound as a yellow foam.

The NMR spectrum of the product (CDCl$_3$) showed absorptions at 7.3 (s, 10H), 5.9 (s, 2H), 5.8–5.2 (m, 3H), 5.1 (s, 2H), 4.4 (s, 1H), 1.5 (s, 3H) and 1.3 (s, 3H) ppm.

EXAMPLE 19

Benzyl 6-(2-Iodomethoxycarbonylamino-2-[4-hydroxyphenyl]acetamido)penicillanate

Using the procedure of Example 18, 3.0 g. of benzyl 6-(2-chloromethoxycarbonylamino-2-[4-hydroxyphenyl]acetamido)penicillanate was treated with sodium iodide in acetone to give 3.19 g. of the title product.

The NMR spectrum of the product (CDCl$_3$) showed absorptions at 7.3 (s, 5H), 7.2 (d, 2H), 6.7 (d, 2H), 5.9 (s, 2H), 5.7–5.2 (m, 3H), 5.2 (s, 2H), 4.4 (s, 1H), 1.5 (s, 3H) and 1.3 (s, 3H) ppm.

EXAMPLE 20

4-Nitrobenzyl 6-(2-Iodomethoxycarbonylamino-2-phenylacetamido)penicillanate

Using the procedure of Example 18, 0.11 g. of 4-nitrobenzyl 6-(2-chloromethoxycarbonylamino-2-phenylacetamido)penicillanate was treated with 0.40 g. of sodium iodide in 5 ml. of acetone, to give 0.11 g. of the title compound.

The NMR spectrum (CDCl$_3$) showed absorptions at 8.2 (d, 2H), 7.5 (d, 2H), 7.3 (s, 5H), 7.0 (d, 1H), 6.4 (d, 1H), 5.9 (s, 2H), 5.6–5.2 (m, 5H), 4.4 (s, 1H), 1.5 (s, 3H) and 1.3 (s, 3H) ppm.

EXAMPLE 21

4-Nitrobenzyl 6-(2-Iodomethoxycarbonylamino-2-[4-hydroxyphenyl]acetamido)penicillanate Reaction of 6-(2-chloromethoxycarbonylamino-2-[4-hydroxyphenyl]acetamido)penicillanate with sodium iodide, using the procedure of Example 18, affords the title compound.

EXAMPLE 22

Benzyl 6-(2-Benzyloxycarbonylamino-2-[4-iodomethoxycarbonyloxyphenyl]acetamido)penicillanate Reaction of 2.0 g. of benzyl 6-(2-benzyloxycarbonylamino-2-[4-chloromethoxycarbonyloxyphenyl]acetamido)penicillanate with 4.4 g. of sodium iodide, according to the procedure of Example 18, afforded 2.1 g. of the title compound.

The NMR spectrum of the title compound (CD$_3$COCD$_3$) showed absorptions at 8.0 (broad d, 1H), 7.6–7.0 (m, 20H), 6.1 (s, 2H), 5.6–5.0 (m, 7H), 4.4 (s, 1H), 1.5 (s, 3H) and 1.3 (s, 3H) ppm.

EXAMPLE 23

4-Nitrobenzyl 6-(2-[4-Nitrobenzyloxycarbonylamino]-2-[4-iodomethoxycarbonyloxyphenyl]acetamido)penicillanate Reaction of 4-nitrobenzyl-6-(2-[4-nitrobenzyloxycarbonylamino]-2-[4-chloromethoxycarbonyloxyphenyl]acetamido)penicillanate with sodium iodide, according to the procedure of Example 18, affords the title compound.

EXAMPLE 24

Benzyl 6-(2-Chloromethoxycarbonylamino-2-phenylacetamido)penicillanate

To a cold (0° C.) suspension of 12.1 g. of benzyl 6-(2-amino-2-phenylacetamido)penicillanate hydrochloride in 250 ml. of tetrahydrofuran was added dropwise, with stirring, 10.4 ml. of diisopropylethylamine. Stirring was continued for 15 minutes then 60 ml. of carbon tetrachloride containing ca. 20 mmoles of chloromethyl chloroformate (together with some methyl chloroformate and some dichloromethyl chloroformate), prepared as described in Preparation 6, was added during approximately 10 minutes. Stirring was continued for one hour, and then the reaction mixture was poured into 1,000 ml. of ethyl acetate. The resulting solution was washed with water and with saturated sodium chloride solution, and then it was dried ($Na_2SO_4$). Concentration of the dried solution in vacuo gave 9.74 g. of a yellow foam. The foam was chromatographed on 480 g. of silica gel using 1:1 hexane-ethyl acetate to give 4.59 g. of the title compound as a foam.

The NMR spectrum ($CDCl_3$) showed absorptions at 7.3 (s, 10H), 5.7 (s, 2H), 5.7–5.2 (m, 3H), 5.2 (m, 3H), 5.2 (s, 2H), 4.4 (s, 1H), 1.5 (s, 3H) and 1.3 (s, 3H) ppm.

EXAMPLE 25

Benzyl 6-(2-Chloromethoxycarbonylamino-2-[4-hydroxyphenyl]acetamido)penicillanate Reaction of 25.3 g. of benzyl 6-(2-amino-2-[4-hydroxyphenyl]acetamido)penicillanate hydrochloride with chloromethyl chloroformate, using the procedure of Example 24, afforded 10.92 g. of the title compound.

The NMR spectrum of the product ($CDCl_3$) showed absorptions at 7.3 (s, 5H), 7.2 (d, 2H), 6.6 (d, 2H), 5.6 (s, 2H), 5.2 (s, 2H), 5.6–5.2 (m, 7H), 4.4 (s, 1H), 1.5 (s, 3H) and 1.3 (s, 3H) ppm.

EXAMPLE 26

4-Nitrobenzyl 6-(2-Chloromethoxycarbonylamino-2-phenylacetamido)penicillanate

Reaction of 5.20 g. of 4-nitrobenzyl 6-(2-amino-2-phenylacetamido)penicillanate hydrochloride with approximately 7 mmol of chloromethyl chloroformate, using the procedure of Example 24, afforded 2.25 g. of the title compound.

The NMR spectrum of the title compound ($CDCl_3$) showed absorptions at 8.2 (d, 2H), 7.3 (s, 5H), 7.2 (d, 2H), 6.8 (d, 1H), 6.4 (d, 1H), 5.7–5.2 (m, 7H), 5.55 (s, 2H), 5.2 (s, 2H), 4.4 (s, 1H), 1.5 (s, 3H) and 1.3 (s, 3H) ppm.

EXAMPLE 27

4-Nitrobenzyl 6-(2-Chloromethoxycarbonylamino-2-[4-hydroxyphenyl]acetamido)penicillanate Reaction of 4-nitrobenzyl 6-(2-amino-2-[4-hydroxyphenyl]acetamido)penicillanate hydrochloride with chloromethyl chloroformate, using the procedure of Example 24, affords the title compound.

EXAMPLE 28

Benzyl 6-(2-Benzyloxycarbonylamino-2-[4-chloromethoxycarbonyloxyphenyl]acetamido)penicillanate A solution of approximately 12 mmol of chloromethyl chloroformate in 60 ml. of carbon tetrachloride, prepared as described in Preparation 6, was added dropwise, with stirring to an ice-cold solution of 6.8 g. of benzyl 6-(2-benzyloxycarbonylamino-2-[4-hydroxyphenyl]acetamido)penicillanate and 4.0 g. of pyridine in 100 ml. of tetrahydrofuran. Stirring was continued for one hour and then 300 ml. of chloroform was added. The resulting mixture was washed with water, with 1 N hydrochloric acid and with saturated sodium chloride solution. The resulting organic solution was dried ($Na_2SO_4$) and then it was evaporated in vacuo. The residue was chromatographed on 350 g. of silica gel, eluting with 3:2 hexane-ethyl acetate, to give 2.0 g. of the title compound.

The NMR spectrum of the title product ($CD_3COCD_3$) showed absorptions at 7.4 and 7.3 (2 singlets on a broad base, 14H), 6.0–5.0 (m, with singlets showing at 6.0, 5.2 and 5.0, 9H), 4.4 (s, 1H), 1.5 (s, 3H) and 1.3 (s, 3H) ppm.

EXAMPLE 29

4-Nitrobenzyl 6-(2-[4-Nitrobenzyloxycarbonylamino]-2-[4-chloromethoxycarbonyloxyphenyl]acetamido)penicillanate Reaction of 4-nitrobenzyl 6-(2-[4-nitrobenzyloxycarbonylamino]-2-[4-hydroxyphenyl]acetamido)penicillanate with chloromethyl chloroformate, using the procedure of Example 28, affords the title compound.

PREPARATION 1

Benzyl 6-(2-Amino-2-phenylacetamido)penicillanate Hydrochloride

To a stirred mixture of 37.8 g. of potassium carbonate and 58.1 g. of methyl acetoacetate in 500 ml. of N,N-dimethylformamide was added 100 g. of 6-(2-amino-2-phenylacetamido)penicillanic acid trihydrate (ampicillin trihydrate). Stirring was continued for two hours, and then 51.3 g. of benzyl bromide was added during two minutes. Stirring was continued for a further two hours and then the reaction mixture was poured into a mixture of 2,000 ml. of ethyl acetate and 200 ml. of water. The layers were separated and the organic layer was washed with water followed by saturated sodium chloride solution. The organic layer was dried ($Na_2SO_4$) and then evaporated in vacuo to give 138 g. of a yellow oil. This oil was dissolved in 500 ml. of acetone, 500 ml. of water and 100 ml. of 2 N hydrochloric acid. The mixture was stored for 10 minutes (pH=1.5), and then it was filtered and the acetone was removed by evaporation in vacuo. The aqueous residue was washed with diethyl ether, saturated with sodium chloride, and then extracted with ethyl acetate. The extract was dried ($Na_2SO_4$), concentrated to about 200 ml., and then added with stirring to 200 ml. of diethyl ether. The solid which formed was filtered off, triturated under diethyl ether, and dried under high vacuum to give 85 g. of the title compound.

The NMR spectrum of the title compound ($CD_3COCD_3$) showed absorptions at 7.3 (s, 10H), 5.1 (s, 2H), 4.4 (s, 1H), 1.4 (s, 3H) and 1.2 (s, 3H) ppm.

PREPARATION 2

Benzyl 6-(2-Amino-2-[4-hydroxyphenyl]acetamido)penicillanate Hydrochloride 6-(2-Amino-2-[4-hydroxyphenyl]acetamido)penicillanic acid trihydrate (amoxicillin trihydrate) (100 g.) was converted into its benzyl ester using the method of Preparation 1. The yield was 25.3 g.

The NMR spectrum of the product showed absorptions at 9.9 (broad s, 1H), 9.2 (broad d, 1H), 8.7 (broad s, 3H), 7.4 (s, 5H), 7.3 (d, 2H), 6.8 (d, 2H), 5.8–5.0 (m, 5H), 4.3 (s, 1H), 1.5 (s, 3H) and 1.3 (s, 3H) ppm.

PREPARATION 3

4-Nitrobenzyl 6-(2-Amino-2-phenylacetamido)penicillanate Hydrochloride

To a stirred solution of 22.6 g. of potassium 6-(2-[2-methoxycarbonyl-1-methylvinylamino]-2-phenylacetamido)penicillanate in 150 ml. of N,N-dimethylformamide, at ca. 0° C., was added 10.8 g. of 4-nitrobenzyl bromide. Stirring was continued for 10 minutes at ca. 0° C., followed by 45 minutes at room temperature. The reaction mixture was then poured into a stirred mixture of 600 ml. of ethyl acetate and 100 ml. of saturated sodium chloride solution. The organic phase was removed, washed with water, washed with saturated sodium chloride solution, dried using sodium sulfate and evaporated in vacuo. This afforded 32 g. of a viscous oil. This oil was dissolved in a mixture of 300 ml. of ethyl acetate, 150 ml. of water and 150 ml. of n-butanol. Sufficient 4 N hydrochloric acid was added to achieve a pH of 2.5 and thereafter additional acid was added to maintain the pH at 2.5. After 2¼ hours the pH had stabilized at 2.5. At this point, the reaction mixture was diluted with 500 ml. of water and extracted with diethyl ether. The aqueous phase was saturated with sodium chloride and then it was extracted with dichloromethane. The extracts were dried (Na2SO4) and then concentrated in vacuo to give 17.7 g. of the title compound.

The NMR spectrum of the title compound (DMSO-d6) showed absorptions at 9.5 (broad d, 1H), 9.0 (broad s, 3H), 8.2 (d, 2H), 7.6 (d, 2H), 7.4 (broad s, 5H), 5.7–5.0 (m, 5H), 4.4 (s, 1H), 1.5 (s, 3H) and 1.3 (s, 3H) ppm.

4-Nitrobenzyl 6-(2-amino-2-[4-hydroxyphenyl]acetamido)penicillanate hydrochloride can be obtained using the above procedure, but substituting potassium 6-(2-[2-methoxycarbonyl-1-methylvinylamino]-2-[4-hydroxyphenyl]acetamido)penicillanate for the potassium 6-(2-[2-methoxycarbonyl-1-methylvinylamino]-2-phenylacetamido)penicillanate.

PREPARATION 4

Benzyl 6-(2-Benzyloxycarbonylamino-2-[4-hydroxyphenyl]acetamido)penicillanate

Using 2 N sodium hydroxide, the pH of a solution of 9.8 g. of benzyl 6-(2-amino-2-[4-hydroxyphenyl]acetamido)penicillanate in 60 ml. of acetone and 60 ml. of water was adjusted to 8.5, with stirring, and then benzyl chloroformate was added dropwise, with the pH being maintained between 7 and 8. Stirring was continued until the pH stabilized at 7.5. At this point, 200 ml. of ethyl acetate was added, and then the layers were separated and the aqueous phase further extracted with ethyl acetate. The combined ethyl acetate solutions were washed with 1 N hydrochloric acid, with water and then with saturated sodium chloride solution. The ethyl acetate solution was then dried using sodium sulfate and concentrated in vacuo to give 10 g. of the title compound.

The NMR of the compound (CD3COCD3) showed absorptions at 7.4–6.8 (2 s's and 2 d's, 14H), 5.8–5.0 (m, 3H), 5.2 (s, 2H), 4.4 (s, 1H), 1.6 (s, 3H) and 1.4 (s, 3H) ppm.

4-Nitrobenzyl 6-(2-[4-nitrobenzyloxycarbonylamino]-2-[4-hydroxyphenyl]acetamido)penicillanate can be obtained from 4-nitrobenzyl 6-(2-amino-2-[4-hydroxyphenyl]acetamido)penicillanate and 4-nitrobenzyl chloroformate, using the above procedure.

PREPARATION 5

Tetrabutylammonium Penicillanate 1,1-Dioxide

To a stirred solution of 2.55 g. of sodium penicillanate 1,1-dioxide in 20 ml. of water was added 3.80 g. of tetrabutylammonium bisulfate. Stirring was continued for 5 minutes and then 20 ml. of chloroform was added. The pH was adjusted to 6.8 with saturated aqueous sodium bicarbonate and then the aqueous layer was saturated with sodium sulfate. The layers were separated and the aqueous layer was extracted with chloroform. The combined chloroform solutions were dried using sodium sulfate and then evaporated in vacuo to give the tetrabutylammonium salt of penicillanic acid 1,1-dioxide.

The tetrabutylammonium salt of 6-beta-hydroxymethylpenicillanic acid 1,1-dioxide can be prepared in a similar manner.

PREPARATION 6

Chloromethyl Chloroformate

To a solution of 2.16 g. of chlorine in 50 ml. of degassed carbon tetrachloride at ca. −10° C. was added 3.79 g. of methyl chloroformate. The solution was irradiated with a 125 watt tungsten light bulb until the yellow color had been discharged. Analysis of the carbon tetrachloride solution at this point by nuclear magnetic resonance spectroscopy revealed that it contained chloromethyl chloroformate, methyl chloroformate and dichloromethyl chloroformate in the molar ratio 64:30:6.

PREPARATION 7

6-alpha-Hydroxymethylpenicillanic Acid 1,1-Dioxide

A. benzyl 6-bromo-6-hydroxymethylpenicillanate

A solution of 44.9 g. of benzyl 6,6-dibromopenicillanate in 600 ml. of dry tetrahydrofuran was cooled to −78° C. and 56.4 ml. of t-butylmagnesium chloride was added dropwise with vigorous stirring under an inert atmosphere while maintaining the temperature at −60° C. After stirring 30 minutes at −78° C., the solution was treated with gaseous formaldehyde in a stream of nitrogen until five molar equivalents had been added. The reaction was quenched at −78° C. by the addition of 5.7 ml. of acetic acid, dropwise, over a period of 25 minutes. The reaction solution was allowed to warm to room temperature and was concentrated in vacuo. To the residue was added 200 ml. of water and 200 ml. of ethyl acetate. The organic layer was separated and the water layer extracted again with ethyl acetate. The organic phases were combined, washed successively with water (200 ml.), 5% aqueous sodium bicarbonate (200 ml.) and brine (200 ml.) and dried over magnesium sulfate. Removal of the solvent under reduced pressure provided 38.2 g. of the desired product, as a mixture of epimers at C-6.

B. benzyl 6-bromo-6-hydroxymethylpenicillanate 1,1-dioxide

To a solution of 500 mg. of benzyl 6-bromo-6-hydroxymethylpencillanate in 30 ml. of methylene chloride, cooled in an ice bath to 0°-5° C., was added portionwise 633 mg. of 85% m-chloroperbenzoic acid over a period of 20 minutes. The reaction mixture was allowed to warm to room temperature and allowed to stir for about 40 minutes. The solvent was removed in vacuo and the residue treated with water and ethyl acetate. The pH of the mixture was adjusted to 7.4 with a saturated sodium bicarbonate solution, and the organic phase separated and treated with 30 ml. of fresh water. The pH of the mixture was adjusted to 8.2 with saturated sodium bicarbonate and the ethyl acetate layer separated and washed with a saturated sodium bicarbonate solution and a brine solution. The ethyl acetate layer was separated, dried over magnesium sulfate and evaporated to an oil, 500 mg.

C. 6-alpha-hydroxymethylpenicillanic acid 1,1-dioxide

A suspension of 500 mg. of 5% palladium-on-charcoal and 500 mg. of benzyl 6-bromo-6-hydroxymethyl-penicillanate 1,1-dioxide in 200 ml. of 50% water-methanol was shaken in a hydrogen atmosphere at an initial pressure of 48 psi for 20 minutes. An additional 500 mg. of fresh catalyst was added and the hydrogen pressure adjusted to 51 psi. After one hour of shaking the catalyst was filtered and the methanol removed in vacuo. The pH of the residual solution was adjusted to 8.0 and extracted with ethyl acetate. The aqueous layer was acidified to pH 2 with 6 N hydrochloric acid and the product extracted with ethyl acetate. Removal of the solvent gave 100 mg. of the desired product, which was crystallized from chloroform-ethyl acetate containing a drop of dimethyl sulfoxide, m.p. 211°-212° C. (dec.).

The NMR (100 MHz) spectrum (DMSO-d$_6$) showed absorption at 4.93 (d, 1H, J=2 Hz), 4.27 (s, 1H), 3.76 (m, 3H), 1.5 (s, 3H) and 1.4 (s, 3H) ppm.

I claim:
1. A compound of the formula

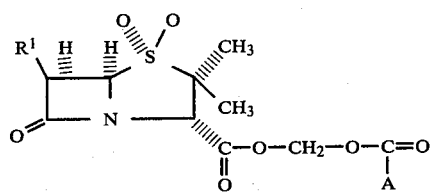

the pharmaceutically-acceptable acid addition salts thereof and the pharmaceutically-acceptable base salts thereof; wherein
R$^1$ is selected from the group consisting of hydrogen and hydroxymethyl; and
A is selected from the group consisting of

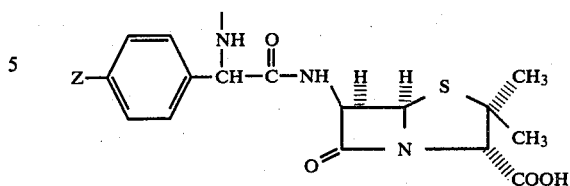

and

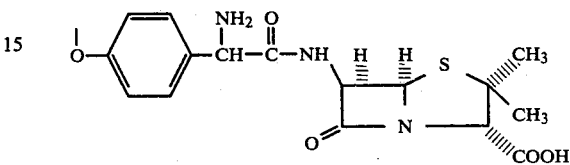

wherein Z is selected from the group consisting of hydrogen and hydroxy.

2. A compound according to claim 1, wherein R$^1$ is hydrogen.

3. The compound according to claim 2, wherein A is

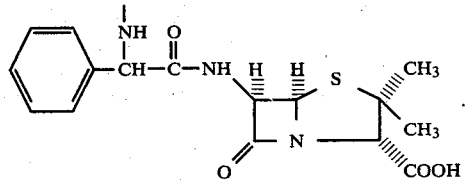

4. The compound according to claim 2, wherein A is

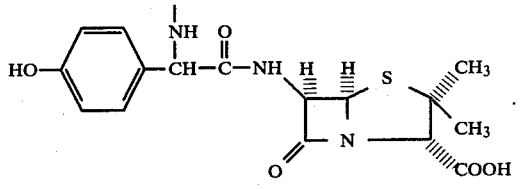

5. The compound according to claim 2, wherein A is

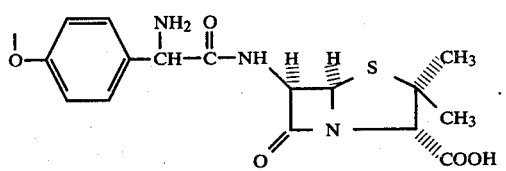

6. A compound according to claim 1, wherein R$^1$ is hydroxymethyl.

7. The compound according to claim 6, wherein A is

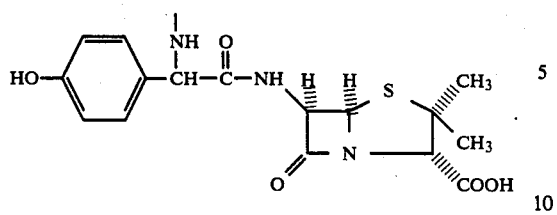

8. A method of treating a bacterial infection in a mammalian subject, which comprises administering to said subject an antibacterially effective amount of a compound of the formula

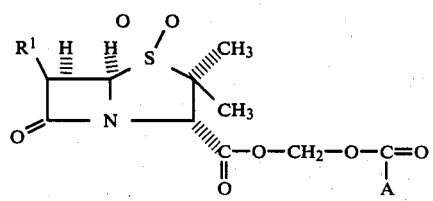

a pharmaceutically-acceptable acid addition salt thereof or a pharmaceutically-acceptable base salt thereof; wherein $R^1$ is selected from the group consisting of hydrogen and hydroxymethyl; and A is selected from the group consisting of

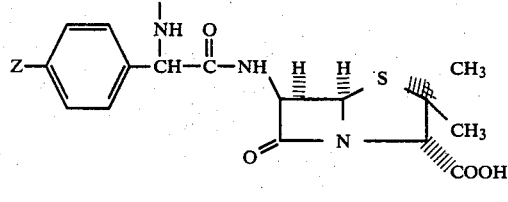

and

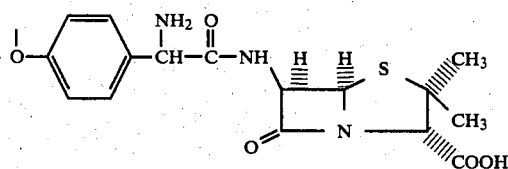

wherein Z is selected from the group consisting of hydrogen and hydroxy.

9. The method according to claim 8, wherein $R^1$ is hydrogen.

10. The method according to claim 9, wherein A is

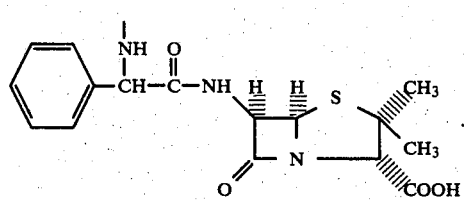

11. The method according to claim 9, wherein A is

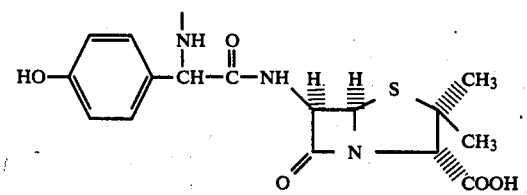

12. The method according to claim 9, wherein A is

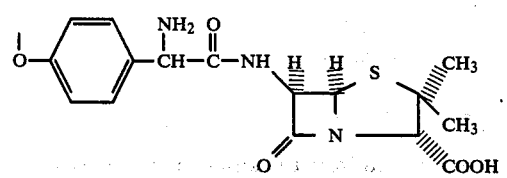

13. The method according to claim 8, wherein $R^1$ is hydroxymethyl.

14. The method according to claim 13, wherein A is

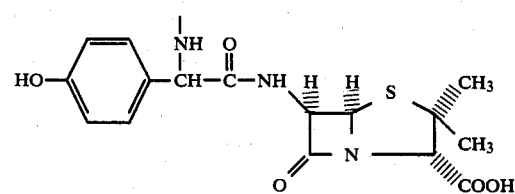

15. A pharmaceutical composition, suitable for treating a bacterial infection in a mammalian subject, which comprises an antibacterially effective amount of a compound according to claim 1 and a pharmaceutically-acceptable carrier.

16. A compound of the formula

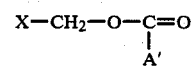

wherein

X is selected from the group consisting of chloro and iodo; and A' is selected from the group consisting of

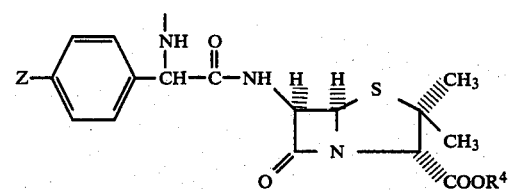

and

-continued

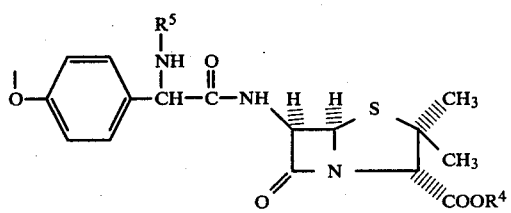

wherein

R⁴ is selected from the group consisting of benzyl and 4-nitrobenzyl;

R⁵ is selected from the group consisting of benzyloxycarbonyl and 4-nitrobenzyloxycarbonyl; and Z is selected from the group consisting of hydrogen and hydroxy.

17. A compound according to claim 16, wherein A' is

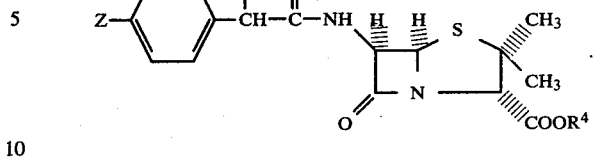

18. The compound according to claim 17, wherein Z is hydrogen and R⁴ is benzyl.

19. The compound according to claim 17, wherein Z is hydrogen and R⁴ is 4-nitrobenzyl.

20. The compound according to claim 17, wherein Z is hydroxy and R⁴ is benzyl.

21. The compound according to claim 16, wherein A' is

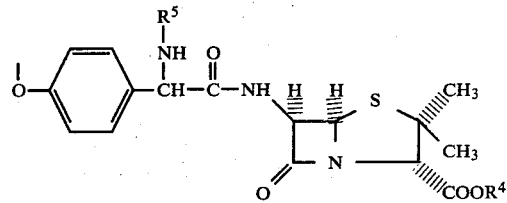

wherein R⁴ is benzyl and R⁵ is benzyloxycarbonyl.

* * * * *

UNITED STATES PATENT AND TRADEMARK OFFICE
CERTIFICATE OF CORRECTION

PATENT NO. : 4,377,590
DATED : March 22, 1983
INVENTOR(S) : Robert F. Myers

It is certified that error appears in the above-identified patent and that said Letters Patent are hereby corrected as shown below:

Column 21, lines 15 to 20, that portion of the formula reading 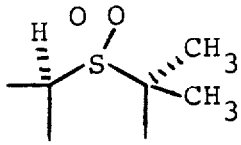 should read 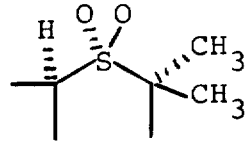 .

Column 21, lines 35 to 40, that portion of the formula reading 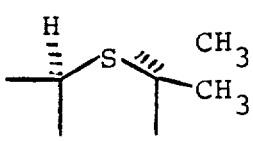 should read 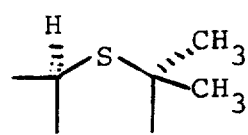 .

Signed and Sealed this

Twenty-first Day of June 1983

|SEAL|

Attest:

DONALD J. QUIGG

Attesting Officer

Acting Commissioner of Patents and Trademarks